Figure 1:
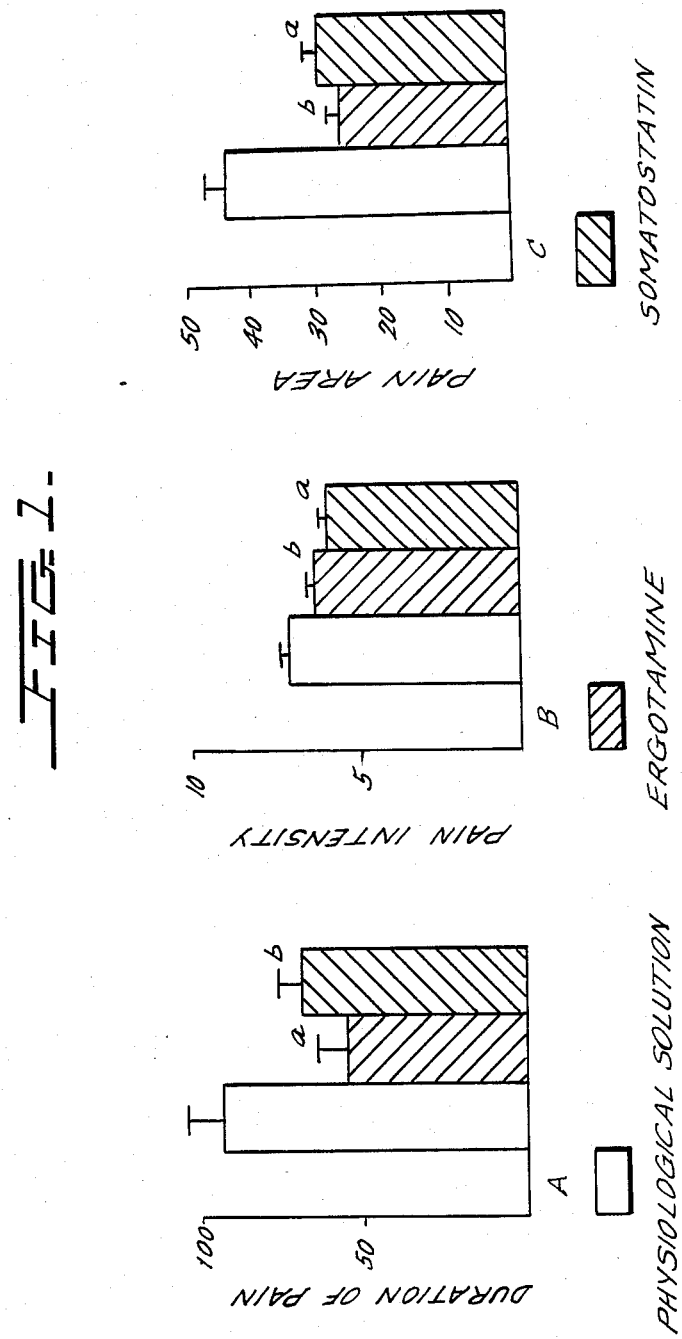

United States Patent [19]

Sicuteri

[11] Patent Number: 4,493,830

[45] Date of Patent: Jan. 15, 1985

[54] METHOD FOR THE TREATMENT OF IDIOPATHIC HEADACHE ATTACKS, IN PARTICULAR MIGRAINE AND CLUSTER HEADACHE

[75] Inventor: Federigo Sicuteri, Florence, Italy

[73] Assignee: Istituto Farmacologico Serono of Rome, Italy

[21] Appl. No.: 604,133

[22] Filed: Apr. 26, 1984

[30] Foreign Application Priority Data

May 4, 1983 [IT] Italy .............................. 48225 A/83

[51] Int. Cl.³ ..................... A61K 37/00; C07C 103/52
[52] U.S. Cl. .............................. 424/177; 260/112.5 S
[58] Field of Search .................. 424/177; 260/112.5 S

[56] References Cited

U.S. PATENT DOCUMENTS 3,842,067 10/1974 Sarantakis ..................... 260/112.5 S Primary Examiner—Delbert R. Phillips
Attorney, Agent, or Firm—Ostrolenk, Faber, Gerb & Soffen

[57] ABSTRACT

Idiopathic headaches are treated with somatostatin.

6 Claims, 3 Drawing Figures

METHOD FOR THE TREATMENT OF IDIOPATHIC HEADACHE ATTACKS, IN PARTICULAR MIGRAINE AND CLUSTER HEADACHE

SUMMARY

The method for treatment of idiopathic headache attacks consists in the administration of an efficacious therapeutical quantity of Somatostatin.

The present invention relates to a method of treatment for idiopathic headache attacks, particularly migraine and cluster headache.

Idiopathic headache conventionally means the painful syndromes localized in the head, which cannot be attributed to documentable "peripheric" mechanism (inflammations, aneurisms, tumours). Such headaches are called idiopathic in that the mechanism of the syndrome is still unknown. Interpretations like, vascular and muscular tension, according to United States investigators, and "central" due to an impaired nociceptive system, according to Italian investigators, are hypotheses still awaiting confirmation.

The idiopathic pain syndromes can occur in attacks of 1-2 days, like common migraine, or in attacks of 1-2 hours daily with great intensity, as in the case of cluster headache.

Symptomatic treatment of single attacks is based on parenteral, oral and rectal administration of Ergotamine Tartrate at doses of 0.25-0.5 mg.

Given the violence and relatively brief duration of the headaches, administration of Ergotamine must be made parenterally to be efficacious.

Use of Ergotamine is limited or refused due to the frequence of side effects i.e. nausea, vomiting, and less frequently, hypotensive collapse phenomena.

Ergotamine is usually controindicated in arteriopathy, especially in cases of ischemic cardiopathy, coronary diseases, and cerebrovascular dieases.

Somatostatin is a peptidic hormone, originally studied for its inhibitory effect on the hypophyseal somatotropin hormone, also known as Somatotrophin.

Therefore, Somatostatin is frequently known as SRIF (Somatotropin Release Inhibiting Factor).

Recent studies have shown that Somatostatin is capable of inhibiting gastric secretion, pancreatic endocrine secretion, glucagon secretion and of reducing the blood flow in the splanchnic area without determining significant variations in arterial pressure.

Even more recently, the inhibitory effect of Somatostatin on the excretion of the Somatotropin hormone was linked with the known therapeutic effect of Somatostatin in severe cases of psoriasis. However, its real mechanism is still the object of further studies.

Somatostatin was originally isolated from bovine and ovine hypothalamus and has a well-known structural formula; it is currently reproduced by chemical synthesis.

The cyclic tetradecapeptide structure of Somatostatin is as follows:

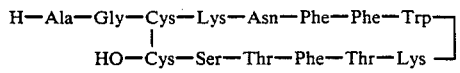

The principal aim of the present invention is to provide a therapeutic method for the treatment of idiopathic headache attacks that consists in the administration of Somatostatin. Administration of Somatostatin has been shown to be particularly advantageous in migraine and cluster headache. Somatostatin is usually administered by venous infusion. The same route of administration was employed in the experiments leading to the present invention, with doses varying from 100 to 500 mcg, administered by slow intravenous injection or phlebo. Satisfactory results have also been obtained by intramuscular or subcutaneous injections of Somatostatin at comparable doses.

The effect of Somatostatin administered by venous infusion was compared with placebo (physiological solution) and Ergotamine, the drug most active, at present, in the treatment of migraine and cluster headache attacks and usually administered via the i.m. route.

Six consenting patients, suffering from cluster headache, were hospitalized. Two presented with a chronic state (more than one year) while the other four were in an attack stage at the moment of entering hospital. The patients received no other pharmaceuticals during the four days prior to commencing the study.

In each patient attacks lasted an average of 1-2 hours. All patients showed, to a greater or lesser degree, the usual neurovegetative symptoms, homolateral to the side affected by the pain syndrome.

At the beginning of the attack, 10 minutes after the onset of pain, the patients received one of the following treatments:

(a)

50 ml physiological solution i.v.;
1 ml physiological solution i.m.;

(b)

500 mcg Somatostatin in 50 ml physiological solution, i.v.;
1 ml physiological solution i.m.;

(c)

50 ml physiological solution i.v.;
250 mcg Ergotamine Tartrate in 1 ml physiological solution i.m.

Duration of venous infusion was 20 minutes (50 drops per min.), and was started simultaneously with the i.m. injection. Treatments and patients were randomized and the trial was carried out in double blind.

In total, 9 attacks were treated for each patient, who received treatments (a) (b) or (c) 3 times; in this way, each treatment was used 18 times.

Pain intensity was ascertained every 10 minutes on a visible scale. Values were recorded on the ordinate against the time which was recorded on the abscissa.

3 parameters were used for statistical assessment; maximum intensity of pain expressed in arbitrary units; duration of pain expressed in minutes; area below the curve expressed in arbitrary units. During infusion with Somatostatin, blood pressure and pulse rates were recorded every 10 minutes for an hour.

Duration of pain, which resulted 93±10 minutes following administration of physiological solution, was reduced with Ergotamine treatment to 55±8 minutes and with Somatostatin treatment to 68±7 minutes (see FIG. 1A).

Ergotamine and Somatostatin reduced pain duration by 41 and 27% respectively as compared with placebo.

Maximum pain intensity (expressed in arbitrary units) obtained after injection of physiological solution resulted 7.1±0.3 arbitrary units; after administration of Somatostatin it resulted 5.9±0.2 arbitrary units, and after administration of Ergotamine, 6.2±0.3 arbitrary units. (see FIG. 1B).

Somatostatin and Ergotamine reduced maximum pain intensity by 17% and 13% respectively.

The area under the pain curve (expressed in arbitrary units), after administration of physiological solution, was 43.8±6.2 arbitrary units, and was reduced to 23.3±3.1 and 29.3±3.4 respectively by administration of Ergotamine and Somatostatin (see FIG. 1C). Therefore, Ergotamine and Somatostatin reduced the pain area by 47% and 34% respectively.

Among the values obtained after Ergotamine and Somatostatin administration, no statistically significant difference was shown, nor were there significant variations in blood pressure or pulse rates during infusion with Somatostatin.

From the trial described above it may be concluded that Somatostatin is significantly more efficacious than placebo in reducing pain during attacks of cluster headache, and slightly less active, but not significantly so, than Ergotamine, considered today as the most efficacious pharmaceutical in the treatment of such conditions.

On the other hand, it is important to consider the minor incidence of side-effects in the case of Somatostatin as compared with Ergotamine and also the minor entity of contraindications regarding Somatostatin as compared with Ergotamine.

In uncontrolled trails conducted with fewer patients, Somatostatin was efficacious when administered as 100 mcg in a bolus i.v. injection, at doses of 250 mcg, i.m. and s.c., as well as the classical administration via venous infusion at doses of 500 mcg.

Obviously, many modifications and variations to the therapeutic schedule described above could be effected without departing from the spirit and sphere of the invention.

The examples supplied are intended to illustrate and not limit the invention.

I claim:

1. Method for the treatment of idiopathic headache attacks characterized by the fact of administering a therapeutically efficacious quantity of Somatostatin.

2. Method according to claim 1, characterized by the fact that migraine or cluster headache are treated.

3. Method according claim 1, characterized by the fact that Somatostatin is administered by venous infusion or i.v. injection.

4. Method according to claim 1, characterized by the fact that Somatostatin is administered by i.m. injection.

5. Method according to claim 1, characterized by the fact that Somatostatin is administered by s.c. injection.

6. Method according to any prior claims characterized by the fact that Somatostatin is administered at doses of 100 to 500 mcg.